United States Patent
Ren et al.

(10) Patent No.: US 12,127,578 B2
(45) Date of Patent: Oct. 29, 2024

(54) MICROENCAPSULED CONJUGATED LINOLEIC ACID GLYCERIDE POWDER AND PREPARATION METHOD THEREOF

(71) Applicant: INNOBIO CORPORATION LIMITED, Liaoning (CN)

(72) Inventors: Xiang Ren, Liaoning (CN); Yutao Xu, Liaoning (CN); Zhongle Tian, Liaoning (CN); Jianbin Chen, Liaoning (CN); Wenzhong Wu, Liaoning (CN)

(73) Assignee: INNOBIO CORPORATION LIMITED, Liaoning (CN)

( * ) Notice: Subject to any disclaimer, the term of this patent is extended or adjusted under 35 U.S.C. 154(b) by 873 days.

(21) Appl. No.: 17/260,143

(22) PCT Filed: Oct. 26, 2018

(86) PCT No.: PCT/CN2018/111993
§ 371 (c)(1),
(2) Date: Jan. 13, 2021

(87) PCT Pub. No.: WO2020/010752
PCT Pub. Date: Jan. 16, 2020

(65) Prior Publication Data
US 2021/0315253 A1    Oct. 14, 2021

(30) Foreign Application Priority Data
Jul. 13, 2018    (CN) .......................... 201810772425.2

(51) Int. Cl.
| A23P 10/30 | (2016.01) |
| A23L 29/00 | (2016.01) |
| A23L 29/30 | (2016.01) |
| A23L 33/12 | (2016.01) |

(52) U.S. Cl.
CPC ............... *A23P 10/30* (2016.08); *A23L 29/04* (2016.08); *A23L 29/30* (2016.08); *A23L 33/12* (2016.08)

(58) Field of Classification Search
CPC ...................................................... A23P 10/30
See application file for complete search history.

(56) References Cited

FOREIGN PATENT DOCUMENTS

| CN | 1357408 A | | 7/2002 |
| CN | 104054849 A | | 9/2014 |
| CN | 104304838 A | * | 1/2015 |
| CN | 104544092 A | | 4/2015 |
| CN | 106343577 A | * | 1/2017 |
| WO | 2017063101 A1 | | 4/2017 |

OTHER PUBLICATIONS

Formal Human Translation of Manjiang et al. CN 1357408. Published 2002. (Year: 2002).*
Konstance et al., "Flow Properties of Spray-Dried Encapsulated Butteroil", Journal of Food Science, vol. 60, No. 4, (1995), pp. 841-844. (Year: 1995).*
Rubio-Rodriguez et al., "Production of omega-3 polyunsaturated fatty acid concentrates: A review", Innovative Food Science and Emerging Technologies, 11, (2010), pp. 1-12. (Year: 2010).*

* cited by examiner

*Primary Examiner* — Elizabeth Gwartney
(74) *Attorney, Agent, or Firm* — NKL Law; Allen Xue

(57) ABSTRACT

The present invention discloses a microencapsuled conjugated linoleic acid glyceride powder and a preparation method thereof. The preparation method comprises the steps of preparing raw materials, preparing an aqueous phase and an oil phase, preparing an emulsion, and spray drying. The raw materials comprise, in parts by mass: 60-85 parts of conjugated linoleic acid glyceride, 5-35 parts of starch or colloid, 4-20 parts of small molecule filler, and 0.01-5 parts of antioxidant.

7 Claims, No Drawings

MICROENCAPSULED CONJUGATED LINOLEIC ACID GLYCERIDE POWDER AND PREPARATION METHOD THEREOF

TECHNICAL FIELD

The present invention belongs to the technical field of microcapsules, and more particularly, relates to a microencapsulated conjugated linoleic acid glyceride powder and a preparation process thereof.

BACKGROUND

In the $21^{st}$ Century, obesity has become an epidemic. Some global estimates made by the World Health Organization in January 2015 are were as follows: in 2014, approximately 13% of adults (11% for men and 15% for women) among approximately 7 billion people worldwide were obese; 39% of adults over the age of 18 (38% for men and 40% for women) are overweight. The global obesity prevalence rate has more than doubled between 1980 and 2014. The United States has the world's largest population of overweight or obese people, with a total of 160 million people. The number of obese people in China has reached 62 million, accounting for 9% of the world's total, ranking second in the world.

Obesity and overweight have become serious threats to public health. Studies have shown that obesity can cause a series of health problems. It is not only a high-risk factor leading to diseases such as diabetes, heart disease, stroke and arthritis, but also related to the increased incidence of pancreatic cancer and other cancers. The problem of obesity not only affects people's quality of life, but also places a heavy burden on the public health service system. In order to reduce the burden of overweight and obesity, the easiest foods and regular physical activities are selected from a healthy perspective. Their effects can be maximized only when people have a healthy lifestyle. Therefore, the food industry can play an important role in promoting balanced nutrition and healthy diet, and providing more and more effective nutrition enhancer products.

Conjugated linoleic acid (CLA) is a series of linoleic acids each having a double bond at positions 9, 11 or 10, 12 of carbon, and geometric isomers. In our daily food intake, the CLA mainly comes from dairy products and beef and mutton. Studies have shown that CLA can increase the activity of carnitine palmitoyl transferase and reduce the activity of lipoprotein lipase. The former functions to promote activity enhancement of fatty acid β-oxidase, thereby accelerating fat burning and reducing the body fat; the latter functions to reduce the activity, thereby reducing the absorption of free fatty acids by fat cells and storing them to form the body fat. In recent years, more and more clinical research data show that CLA has very good performance in weight control. It can accelerate the rate of fat metabolism, so that the fat taken from food enters muscle cells more and becomes energy used; increase the rate of fat degradation in fat cells, reduce the fat already stored in the body, and reduce the body fat; and also reduce the total number of fat cells in the body. While reducing the body fat, CLA also has the effects of avoiding the loss of muscle tissues, forming a virtuous circle, and truly achieving the goals of fat reduction and bodybuilding, and healthy weight loss. In addition to existing in a form of free acids, CLA mainly exists in a form of glyceride, that is, commonly known as conjugated linoleic acid glyceride (CLA TG), which can also achieve the same effect as CLA.

The synthesis methods of conjugated linoleic acid and its glycerides are common in existing patents and literatures, but reports on its microencapsulation technology are rare. This is because the conjugated linoleic acid glyceride is a kind of oils containing 18 carbons and having a conjugated double bond. The difficulty in emulsification of oils having a long carbon chain themselves and the conjugated double bond in the structure make a molecular segment more difficult to bend flexibly, which further increases the difficulty in emulsification. Therefore, there are few reports about the microencapsulation technology of conjugated linoleic acid glyceride at present.

A series of research results related to the microencapsulation of other oils are recorded in the prior art: CN106343577A discloses such a technical solution: dissolving a wall material with appropriate amount of water and pasteurizing the solution, then reducing the temperature to 50 to 60° C. and shearing at a high speed; adding pretreated sea buckthorn oil to make a coarse emulsion with a soluble solid content of 40% or higher; and performing high-pressure homogenization and spray drying to obtain sea buckthorn oil microcapsule powder. The oil load of this microcapsule reaches 48%, and an embedding rate exceeds 97%. The product obtained in this scheme is relatively low in oil load, and the microencapsulation technology used in this scheme is a relatively common technology in the industry, as a result of easy preparation. CN104054849A describes a preparation method, in which advanced technologies such as high-pressure homogeneous emulsification and spray drying are adopted upon formula design and process optimization to perform microencapsulated embedding on medium-chain triglycerides to obtain a high-content medium-chain triglyceride powdered oil, wherein the maximum oil content can reach 80%, and the embedding rate of oil can reach more than 98%. The raw materials used in this patent are medium and long-chain saturated oils, which are easily emulsified and embedded, and the saturated structures of the oils themselves will not be oxidized. The high-temperature emulsification process is adopted in this procedure, which is relatively simple to implement. CN104544092A describes the preparation of microencapsulated linseed oil powder, the formula of which includes a stabilizer, filler, an emulsifier, and an antioxidant; the stabilizer is one or more of gelatin, Arabic gum, and linseed gum. Product performances are not stated in the article. The formula in this patent is complex in components and requires stabilizers to maintain the stability during processing. There are also many patents for microencapsulation of oils, which are basically characterized in that medium and long-chain oils and oils having long-chain non-conjugated structures are subjected to microencapsulated embedding, a high-temperature emulsification and homogenization process is adopted, and emulsifiers, stabilizers and the like are added in most formulas. Foreseeably, in view of the characteristics of conjugated linoleic acid glyceride itself, the preparation of high-quality microencapsulated products will encounter more troubles.

SUMMARY

The present invention aims to provide a microencapsulated conjugated linoleic acid glyceride powder with a high embedding rate and product stability and a preparation method thereof.

Firstly, the preparation method of the microencapsulated conjugated linoleic acid glyceride powder provided by the present invention comprises the following steps:

(1) preparing raw materials, the raw materials containing the following components in parts by mass:

| | |
|---|---|
| conjugated linoleic acid glyceride | 60-85 parts; |
| starch or colloid | 5-35 parts; |
| micromolecule filler | 4-20 parts; |
| antioxidant | 0.01-5 parts; |

(2) dissolving the starch or the colloid and the micromolecule filler in water at 40° C. to 60° C., and then cooling the system to 0-30° C.;

(3) adding an aqueous phase antioxidant into the system in step (2), and stirring at 0° C. to 30° C. until the aqueous phase antioxidant is completely dissolved to obtain an aqueous phase;

(4) adding an oil phase antioxidant into the conjugated linoleic acid glyceride, and stirring at 10°-25° C. until the oil phase antioxidant is completely dissolved to obtain an oil phase;

(5) adding the oil phase into the aqueous phase, controlling the temperature of the system between 0-30° C., shearing and emulsifying the mixture for 0.5 hour to 2 hours, and then homogenizing for 1 time to 3 times at 40-120 MPa to obtain an emulsion; and (6) performing spray drying on the emulsion prepared in step (5) at an air inlet temperature of 90-230° C., and an air outlet temperature of 50-110° C.

The microencapsulated conjugated linoleic acid glyceride powder prepared by the above method is also one of the objects of the present invention.

According to the present invention, the conjugated linoleic acid glyceride is subjected to microcapsulated embedding by means of a low temperature emulsification method which can prevent the oxidation in the process. The microencapsulated conjugated linoleic acid glyceride powder free of allergens and having a high oil load, a high embedding rate, and excellent stability and brewing property may be obtained without adding any emulsifiers and stabilizers.

The present invention breaks through the technical threshold for starch and colloid to be unable to carry out high-capacity conjugated linoleic acid glyceride microencapsulation irrelevant of protein-based wall materials (the first choice for conventional high-load wall materials). All formulas are vegetarian formulas. On this basis, CLA microencapsulated products with high oil load rate and high embedding rate are obtained. The production method is simple and controllable, the whole process is performed at a low temperature, and there is no need to add emulsifiers and stabilizers. The obtained microencapsulated CLA powder has a wide pH adaptability range from pH 1 to 4, is resistant to high temperatures, and can be widely used in baking, solid beverages, capsules, etc.

DETAILED DESCRIPTION

The present invention provides a microencapsulated conjugated linoleic acid glyceride powder and a preparation method thereof. The specific implementation of the method includes the following steps:

(1) preparing raw materials;

(2) dissolving starch or colloid, and small molecule filler in water at 50 to 60° C., and then reducing the temperature of the system to 0 to 20° C.;

(3) adding an aqueous-phase antioxidant to the system in the step (2), and stirring at 0 to 20° C. to be completely dissolved to form an aqueous phase;

(4) adding an oil-phase antioxidant to conjugated linoleic acid glyceride, and stirring at 10 to 20° C. to be completely dissolved to form an oil phase;

(5) adding the oil phase to the aqueous phase, performing shear emulsification for 0.5 to 1.5 h under the condition of controlling the temperature of the system to be 0 to 20° C., and then homogenizing at a high pressure of 45 to 90 MPa for 1 to 3 times to obtain an emulsion; and (6) performing spray drying on the emulsion prepared in the step (5), wherein the inlet air temperature is 110 to 180° C., and the outlet air temperature is 70 to 100° C.

In any of the above-mentioned technical solutions regarding the preparation method, the selection and combination of raw materials is one of the technical means of the present invention to achieve its technical effects.

In one specific implementation, the starch in the raw materials includes raw starch or modified starch, wherein the modified starch is selected from one or a mixture of more of acid modified starch, oxidized starch, octenyl succinate starch ester, starch sodium octenylsuccinate, starch acetate, starch phosphate, cross-linked starch, hydroxypropyl starch, and pregelatinized starch, particularly preferably pregelatinized starch and starch sodium octenylsuccinate. In addition, raw starch is also one of the preferred forms of starch. The colloid is selected from one or a mixture of more of xanthan gum, gelatin and Arabic gum, particularly preferably Arabic gum and gelatin. The results of Embodiments 5 and 6 in this specification have proved that under low temperature conditions, the effects of different wall materials on the embedding performance and the brewing property of the product are substantial. The protein system used in conventional high-load oil is not applicable in the present invention. On the contrary, under the low-temperature conditions of the present invention, only a few starch-based wall materials and some colloid-based wall materials are suitable for use with low-temperature emulsification processes.

In another specific implementation, the small molecule filler involved in the present invention is selected from glucose syrup, maltodextrin, maltooligosaccharide, fructooligosaccharide, resistant dextrin, solid corn syrup, cyclodextrin and the like, particularly preferably maltodextrin, resistant dextrin or maltooligosaccharide.

In yet another implementation, the antioxidants involved in the present invention include an aqueous-phase antioxidant and an oil-phase antioxidant, wherein the aqueous-phase antioxidant is selected from sodium ascorbate, ascorbic acid, citric acid, sodium citrate and ascorbyl palmitate; the oil-phase antioxidant is selected from one or a mixture of more of d-α tocopherol, dl-α tocopherol, hybrid tocopherol, rosemary extract, phospholipid, butyl hydroxyanisole, antioxidant 264, and tert-butyl hydroquinone. The aqueous-phase antioxidant is preferably sodium ascorbate and ascorbic acid. The oil phase antioxidant is preferably selected from hybrid tocopherol, rosemary extract, phospholipid or butylhydroxyanisole.

In still yet implementation of the present invention, the method further comprises a step of adding an anti-caking agent to the microcapsule powder prepared in the step (5), wherein the anti-caking agent is selected from one or a mixture of more of silica, calcium silicate, tricalcium phosphate, and sodium dihydrogen phosphate, preferably silica or calcium silicate. More preferably, the amount of the anti-caking agent should be controlled not to exceed 2% of the mass of the microcapsule powder.

In the technical solution of the present invention, a pretreatment step for the raw materials may also be added to achieve a more excellent effect. Specifically, the pretreatment method includes: mixing activated carbon of 160 to 200 meshes with crude conjugated linoleic acid glyceride according to a mass ratio of 1:(80 to 120) under an operating temperature of 30 to 45° C., stirring for 0.5 to 5 h and performing adsorption, and then filtering with filter cloth of 280 meshes; centrifuging the filtered oils at 10 to 25° C. and 4000 to 6000 rpm for 15-30 min, and taking transparent liquid on the upper layer. The present invention has also been proved by Embodiment 10 that the treated conjugated linoleic acid glyceride is more suitable for low-temperature microencapsulated embedding and the stability of the product is more excellent.

The following non-limitative embodiments are used to further illustrate the technical solutions and effects of the present invention, and should not be construed as limiting the content of the present invention in any form. Unless otherwise specified, the percentages in this specification represent mass percentages.

Embodiment 1

300 g of water is weighed and added into a 1000 mL beaker at a water temperature of 50° C. 75 g of Arabic gum, 25.2 g of maltooligosaccharide and 0.3 g of sodium ascorbate are added and stirred until completely dissolved. The water phase is cooled to 20° C. for later use. 1.5 g of hybrid tocopherol is weighed and mixed with 195 g of conjugated linoleic acid glyceride, and the oil phase is maintained at 20° C. and stirred uniformly. The oil phase is poured into the water phase, subjected to shear emulsification at 20° C. for 1 h, and homogenized twice at a high pressure of 90 MPa. The resulting emulsion is subjected to spray drying, wherein the inlet air temperature is 180° C., and the outlet air temperature is 75° C. The microencapsulated conjugated linoleic acid glyceride powder is obtained, which is named as CLA TG CWD-1.

Embodiment 2

500 g of water is weighed and added into a 2000 mL beaker at a water temperature of 40° C. 100 g of modified starch, 38.1 g of resistant dextrin, 1 g of ascorbic acid and 4 g of sodium ascorbate are added and stirred until completely dissolved. The water phase is cooled to 15° C. for later use. 1.9 g of hybrid tocopherol is weighed and mixed with 350 g of conjugated linoleic acid glyceride, and the oil phase is maintained at 25° C., stirred uniformly and cooled to 15° C. The oil phase is poured into the water phase, subjected to shear emulsification at 15° C. for 1.5 h, homogenized twice at a high pressure of 95 MPa. The resulting emulsion is subjected to spray drying, wherein the inlet air temperature is 170° C., and the outlet air temperature is 84° C. 3 g of calcium silicate is added as an anti-caking agent. The microencapsulated conjugated linoleic acid glyceride powder is obtained, which is named as CLA TG CWD-2.

Embodiment 3

1000 g of water is weighed and added into a 3000 mL beaker at a water temperature of 60° C. 300 g of raw starch, 41 g of maltodextrin, 6.5 g of sodium citrate and 2.5 g of citric acid are added and stirred until completely dissolved. The water phase is cooled to 25° C. for later use. 5 g of rosemary extract is weighed and mixed with 640 g of conjugated linoleic acid glyceride, and the oil phase is maintained at 28° C., stirred uniformly and cooled to 25° C. The oil phase is poured into the water phase, subjected to shear emulsification at 25° C. for 2 h, homogenized for three times at a high pressure of 63 MPa. The resulting emulsion is then subjected to spray drying, wherein the inlet air temperature is 163° C., and the outlet air temperature is 79° C. 5 g of silicon dioxide is added as an anti-caking agent. The microencapsulated conjugated linoleic acid glyceride powder is finally obtained, which is named as CLA TG CWD-3.

Embodiment 4

This embodiment is used to investigate the effects of the emulsification temperature on product properties. The test groups and raw material composition are shown in Table 1.

TABLE 1

| Name | Formula 1 | Formula 2 | Formula 3 | Formula 4 | Formula 5 |
|---|---|---|---|---|---|
| conjugated linoleic acid glyceride | 70% | 70% | 70% | 70% | 70% |
| Modified starch | 15% | | | | |
| Raw starch | | 15% | | | |
| Arabic gum | | | 15% | | |
| Xanthan gum | | | | 15% | |
| Gelatin | | | | | 15% |
| Maltooligosaccharide | 14.8% | 14.8% | 14.8% | 14.8% | 14.8% |
| Sodium ascorbate | 0.1% | 0.1% | 0.1% | 0.1% | 0.1% |
| Phospholipid | 0.1% | 0.1% | 0.1% | 0.1% | 0.1% |

The six formulas in Table 1 above are prepared into microencapsulated conjugated linoleic acid glyceride powder according to the following process flow: water-soluble substances such as modified starch, raw starch, Arabic gum, xanthan gum, gelatin, and maltooligosaccharide are added to water, and stirred at 40° C. until completely dissolved, to prepare an aqueous phase; and sodium ascorbate is added to the aqueous phase and stirred until completely dissolved. The phospholipid is added to the conjugated linoleic acid glyceride at 30° C. and stirred until completely dissolved to prepare an oil phase. The oil phase is poured into the water phase, emulsified at different temperature ranges for 1 h, and homogenized twice at a high pressure of 65 MPa. The spray drying is performed under spray drying conditions in Embodiment) to obtain microencapsulated conjugated linoleic acid glyceride powder under different formulas and different conditions. The embedding rates of the microencapsulated conjugated linoleic acid glyceride powder under different formulas and different conditions are investigated.

Temperature conditions are shown in Table 2:

TABLE 2

| Experiment No. | Temperature range |
|---|---|
| Experiment 1 | 10 ± 3° C. |
| Experiment 2 | 20 ± 3° C. |
| Experiment 3 | 30 ± 3° C. |
| Experiment 4 | 40 ± 3° C. |
| Experiment 5 | 50 ± 3° C. |
| Experiment 6 | 60 ± 3° C. |
| Experiment 7 | 70 ± 3° C. |
| Experiment 8 | 80 ± 3° C. |
| Experiment 9 | 90 ± 3° C. |

The experimental results are shown in Table 3:

TABLE 3

|  | Formula 1 | Formula 2 | Formula 3 | Formula 4 | Formula 5 |
|---|---|---|---|---|---|
| Experiment 1 | 98.3% | 98.3% | 98.2% | 98.4% | 98.1% |
| Experiment 2 | 99.5% | 99.2% | 99.2% | 99.1% | 99.2% |
| Experiment 3 | 98.8% | 98.4% | 98.9% | 98.3% | 98.7% |
| Experiment 4 | 85.4% | 85.3% | 84.2% | 80.3% | 86.7% |
| Experiment 5 | 80.1% | 78.6% | 76.3% | 78.0% | 79.2% |
| Experiment 6 | 72.2% | 73.3% | 70.7% | 73.2% | 74.5% |
| Experiment 7 | 65.6% | 70.2% | 70.1% | 67.7% | 67.6% |
| Experiment 8 | 63.9% | 64.8% | 64.5% | 63.9% | 60.0% |
| Experiment 9 | 60.0% | 62.1% | 61.3% | 59.9% | 54.3% |

It can be seen from the experimental results that when the formulas are the same, the emulsion temperature has a great influence on the embedding rate of the product; when the emulsion temperature is controlled within 30±3° C. and below, the embedding rate of the product is basically above 98%; when the temperature exceeds this range, as the temperature increases, the embedding rate of the product drops sharply. In order to prepare the microencapsulated conjugated linoleic acid glyceride powder having a relatively high load, the emulsion temperature must be controlled to be lower than 30° C., and the emulsion temperature is an important factor in the successful preparation of the product.

Embodiment 5

This embodiment aims to investigate the embedding effects of different wall materials on products under low temperature conditions. The test groups and raw material composition are shown in Table 4.

TABLE 4

| Name | Formula 6 | Formula 7 | Formula 8 | Formula 9 | Formula 10 | Formula 11 | Formula 12 | Formula 13 | Formula 14 |
|---|---|---|---|---|---|---|---|---|---|
| conjugated linoleic acid glyceride | 65% | 65% | 65% | 65% | 65% | 65% | 65% | 65% | 65% |
| Modified starch | 12% | — | — | — | — | — | — | — | — |
| Raw starch | — | 12% | — | — | — | — | — | — | — |
| Arabic gum | — | — | 12% | — | — | — | — | — | — |
| Xanthan gum | — | — | — | 12% | — | — | — | — | — |
| Gelatin | — | — | — | — | 12% | — | — | — | — |
| Sodium caseinate | — | — | — | — | — | 12% | — | — | — |
| Whey protein | — | — | — | — | — | — | 12% | — | — |
| Pea protein | — | — | — | — | — | — | — | 12% | — |
| Soy protein | — | — | — | — | — | — | — | — | 12% |
| Resistant dextrin | 22.8% | 22.8% | 22.8% | 22.8% | 22.8% | 22.8% | 22.8% | 22.8% | 22.8% |
| Sodium ascorbate | 0.1% | 0.1% | 0.1% | 0.1% | 0.1% | 0.1% | 0.1% | 0.1% | 0.1% |
| Phospholipid | 0.1% | 0.1% | 0.1% | 0.1% | 0.1% | 0.1% | 0.1% | 0.1% | 0.1% |

The nine formulas above are prepared into microencapsulated conjugated linoleic acid glyceride powder according to the following process flow: water-soluble substances such as modified starch, raw starch, Arabic gum, xanthan gum, gelatin, sodium caseinate, whey protein, pea protein, soy protein and resistant dextrin are added to the water, stirred at 40° C. until completely dissolved, to prepare an aqueous phase; and sodium ascorbate is then added to the aqueous phase and stirred until completely dissolved, and cooled to 20° C. for later use. The phospholipid is added to the conjugated linoleic acid glyceride at 30° C. and stirred until completely dissolved, and cooled to 20° C. to prepare an oil phase for later use. The oil phase is poured into the water phase, emulsified at 20° C. for 1.5 h, and homogenized twice at a high pressure of 70 MPa. The spray drying is performed by using spray drying conditions in Embodiment 1 to obtain microencapsulated conjugated linoleic acid glyceride powder of different formulas. The embedding rates and the brewing properties of the microencapsulated conjugated linoleic acid glyceride powder of different formulas are investigated.

The experimental results are shown in Table 5:

TABLE 5

| No. | Embedding rate | Brewing property |
|---|---|---|
| Formula 6 | 99.1% | Uniform emulsion |
| Formula 7 | 99.0% | Uniform emulsion |
| Formula 8 | 89.8% | Uniform emulsion |
| Formula 9 | 99.2% | Uniform emulsion |
| Formula 10 | 98.7% | Uniform emulsion |
| Formula 11 | 69.6% | The emulsion is layered with obvious oil slick on the surface |
| Formula 12 | 64.8% | The emulsion is layered with obvious oil slick and clumps on the surface |
| Formula 13 | 70.9% | The emulsion is layered with clumps on the surface and precipitates on the bottom |
| Formula 14 | 68.3% | The emulsion is layered with clumps on the surface and precipitates on the bottom |

It can be seen from the results that the conventionally recognized protein wall materials that can be embedded with high oil load are not suitable for embedding of conjugated linoleic acid glyceride, resulting in a poor effect. In contrast, raw starch, modified starch, Arabic gum, gelatin, and xanthan gum can effectively embed the conjugated linoleic acid glyceride at low temperatures. Therefore, it can also be explained that the emulsion temperature is a key factor affecting the success of microencapsulation, and the type of wall materials is also an important factor.

Embodiment 6

The present invention aims to investigate the applicability of different gums as wall materials under the conditions of the present invention. The test groups and raw material composition are shown in Table 6.

TABLE 6

| Name | Formula 15 | Formula 16 | Formula 17 | Formula 18 | Formula 19 | Formula 20 | Formula 21 |
|---|---|---|---|---|---|---|---|
| conjugated linoleic acid glyceride | 68% | 68% | 68% | 68% | 68% | 68% | 68% |
| Arabic gum | 13% | — | — | — | — | — | — |
| Xanthan gum | — | 13% | — | — | — | — | — |
| Gelatin | — | — | 13% | — | — | — | — |
| Konjac gum | — | — | — | 13% | — | — | — |
| Carrageenan | — | — | — | — | 13% | — | — |
| Agar | — | — | — | — | — | 13% | — |
| Guar gum | — | — | — | — | — | — | 13% |
| Maltodextrin | 18.8% | 18.8% | 18.8% | 18.8% | 18.8% | 18.8% | 18.8% |
| Sodium ascorbate | 0.1% | 0.1% | 0.1% | 0.1% | 0.1% | 0.1% | 0.1% |
| Phospholipid | 0.1% | 0.1% | 0.1% | 0.1% | 0.1% | 0.1% | 0.1% |

The seven formulas above are prepared into microencapsulated conjugated linoleic acid glyceride powder according to the following process flow: water-soluble substances such as Arabic gum, xanthan gum, gelatin, Konjac gum, carrageenan, guar gum, and maltodextrin are added to the water, stirred at 45° C. until completely dissolved, to prepare an aqueous phase; and sodium ascorbate is then added to the aqueous phase and stirred until completely dissolved, and cooled to 18° C. for later use. The phospholipid is added to the conjugated linoleic acid glyceride at 30° C. and stirred until completely dissolved, and cooled to 18° C. to prepare an oil phase for later use. The oil phase is poured into the water phase, emulsified at 18° C. for 1.5 h, and homogenized twice at a high pressure of 80 MPa. The spray drying is performed by using spray drying conditions in Embodiment 1 to obtain microencapsulated conjugated linoleic acid glyceride powder of different formulas. The embedding rates and the brewing properties of the microencapsulated conjugated linoleic acid glyceride powder of different formulas are investigated.

The experimental results are shown in Table 7:

TABLE 7

| No. | Embedding rate | Brewing property | Remarks |
|---|---|---|---|
| Formula 15 | 98.7% | Uniform emulsion | |
| Formula 16 | 99.1% | Uniform emulsion | |
| Formula 17 | 98.4% | Uniform emulsion | |
| Formula 18 | — | — | Unable to powder |
| Formula 19 | 34.9% | The emulsion is layered with oil and clumps on the surface and precipitates on the bottom | |
| Formula 20 | — | — | Unable to powder |
| Formula 21 | 47.6% | The emulsion is layered with oil and clumps on the surface and precipitates on the bottom | |

This experiment investigates the conjugated linoleic acid glyceride embedded with different gums. The results show that not all gums are suitable for the embedding of conjugated linoleic acid glyceride. Only Arabic gum, xanthan gum and gelatin can embed the conjugated linoleic acid glyceride and have a high embedding rate.

Embodiment 7

Formula 6 and Formula 8 in Embodiment 5 are selected. Under the experimental conditions of different temperatures in Embodiment 4, the spray drying conditions in Embodiment 1 are used to obtain multiple sets of products. The stability of the products is investigated, and the results are shown in Table 8:

TABLE 8

| | Formula 6 | | Formula 8 | |
|---|---|---|---|---|
| No. | Initial peroxide value meq/kg | Peroxide value at 60° C./20 days meq/kg | Initial peroxide value meq/kg | Peroxide value at 60° C./20 days Meg/kg |
| Experiment 1 | 0.25 | 2.33 | 0.23 | 2.59 |
| Experiment 2 | 0.24 | 0.72 | 0.23 | 0.70 |
| Experiment 3 | 0.26 | 2.87 | 0.24 | 2.90 |
| Experiment 4 | 0.24 | 5.21 | 0.25 | 4.98 |
| Experiment 5 | 0.27 | 9.03 | 0.26 | 9.37 |

It can be seen from the experimental results that the products prepared by using different temperature process parameters, preferably for two groups of formulas of wall materials, have different stabilities. With respect to the same formula, when the emulsification temperature is 20±3° C., the stability of the product is the best. If the temperature is lower than the above temperature or higher than the above temperature, the stability of the product will be deteriorated to varying degrees. In addition, the higher the temperature, the worse the product stability.

Embodiment 8

CLA TG CWD-1, CLA TG CWD-2 and CLA TG CWD-3 prepared in Embodiments 1 to 3 are respectively investigated in terms of embedding rate, brewing property and high temperature. The results are shown in Table 9:

TABLE 9

| Name | Embedding rate % | Brewing property | Initial peroxide value | Peroxide value at 100° C. 2 h | Peroxide value at 130° C. 2 h | Peroxide value at 160° C. 2 h | Peroxide value at 200° C. 2 h |
|---|---|---|---|---|---|---|---|
| CLA TG CWD-1 | 99.2 | Uniform emulsion | 0.23 meq/kg | 0.32 meq/kg | 0.35 meq/kg | 0.41 meq/kg | 0.53 meq/kg |
| CLA TG CWD-2 | 99.3 | Uniform emulsion | 0.25 meq/kg | 0.31 meq/kg | 0.36 meq/kg | 0.39 meq/kg | 0.49 meq/kg |
| CLA TG CWD-3 | 99.1 | Uniform emulsion | 0.22 meq/kg | 0.28 meq/kg | 0.35 meq/kg | 0.39 meq/kg | 0.48 meq/kg |

As can be seen from the above results, the microencapsulated conjugated linoleic acid glyceride powders CLA TG CWD-1, CLA TG CWD-2 and CLA TG CWD-3 all have higher embedding properties, better preparation properties and excellent high temperature stability.

Embodiment 9

CLA TG CWD-1, CLA TG CWD-2 and CLA TG CWD-3 prepared in Embodiments 1 to 3 are respectively investigated in terms of brewing properties at different pH. The results as shown in FIG. 10.

TABLE 10

| Name | pH 1-3 | pH 4-6 | pH 7 | pH 8-10 | pH 11-14 |
|---|---|---|---|---|---|
| CLA TG CWD-1 | Uniform emulsion | Uniform emulsion | Uniform emulsion | Uniform emulsion | Uniform emulsion |
| CLA TG CWD-2 | Uniform emulsion | Uniform emulsion | Uniform emulsion | Uniform emulsion | Uniform emulsion |
| CLA TG CWD-3 | Uniform emulsion | Uniform emulsion | Uniform emulsion | Uniform emulsion | Uniform emulsion |

As can be seen from the above results, the microencapsulated conjugated linoleic acid glyceride powders CLA TG CWD-1, CLA TG CWD-2 and CLA TG CWD-3 all have excellent acid and alkali resistance, and can be normally brewed in different pH ranges.

Embodiment 10

The conjugated linoleic acid glyceride is extracted with a supercritical $CO_2$ method. When a refrigeration unit is turned on and the $CO_2$ temperature is reduced to 0° C., corn oil or safflower oil is poured into the bottom of a rectification tower. A temperature gradient is set into 10 to 15° C. and a pressure into 10 to 20 MPa. The extract is collected every 10 min by introducing $CO_2$ to obtain crude conjugated linoleic acid glyceride. The prepared crude conjugated linoleic acid glyceride is heated and stirred for adsorption treatment with activated carbon having a granularity of 160 to 200 meshes. The activated carbon and the crude conjugated linoleic acid glyceride are mixed at 30 to 45° C. in a mass ratio of 1:(80 to 120), then stirred for 0.5 to 5 hours for adsorption, and filtered with filter cloth of 280 meshes. Then, the filtered oils are centrifuged at 10 to 25° C. and 4000 to 6000 rpm for 15 to 30 minutes, and the upper transparent liquid is taken as conjugated linoleic acid glyceride (treated). At the same time, the conjugated linoleic acid glyceride extracted only by the supercritical $CO_2$ method is defined as conjugated linoleic acid glyceride (untreated).

The treated conjugated linoleic acid glyceride and the untreated conjugated linoleic acid glyceride are respectively treated with Formula 1 in Embodiment 4 and subjected to microencapsulated embedding under different emulsification temperature conditions in Experiments 1 to 9 to obtain a product 1 (treated) and a product 2 (untreated). The comparison results are shown in Table 11:

TABLE 11

| | Product 1 (treated) | | | Product 2 (untreated) | | |
|---|---|---|---|---|---|---|
| No. | Embedding rate | Initial peroxide value meq/kg | Peroxide value at 60° C. 2 h meq/kg | Embedding rate | Initial peroxide value meq/kg | Peroxide value at 60° C. 2 h meq/kg |
| Experiment 1 | 98.5% | 0.28 | 2.51 | 98.1% | 0.31 | 3.49 |
| Experiment 2 | 99.5% | 0.27 | 0.66 | 99.0% | 0.29 | 2.19 |
| Experiment 3 | 98.1% | 0.28 | 2.99 | 98.6% | 0.28 | 4.03 |
| Experiment 4 | 84.4% | 0.26 | 5.62 | 80.3% | 0.29 | 7.66 |
| Experiment 5 | 80.1% | 0.27 | 9.24 | 79.2% | 0.30 | 12.05 |
| Experiment 6 | 72.9% | 0.25 | 10.17 | 68.8% | 0.32 | 15.81 |
| Experiment 7 | 65.7% | 0.29 | 13.28 | 61.2% | 0.34 | 20.02 |
| Experiment 8 | 63.3% | 0.26 | 13.64 | 56.3% | 0.29 | 21.34 |
| Experiment 9 | 59.0% | 0.26 | 16.07 | 48.4% | 0.28 | 25.89 |

As can be seen from the results, the treated conjugated linoleic acid glyceride is more suitable for low-temperature microencapsulated embedding and the stability of the product is more excellent.

The invention claimed is:

1. A method for preparing a microencapsulated conjugated linoleic acid glyceride powder, comprising
step 1: preparing raw materials containing the following components in parts by mass, based on a total mass of the raw materials of 100 parts:

| | |
|---|---|
| conjugated linoleic acid glyceride | 60-85 parts; |
| starch or colloid | 5-35 parts; |
| micromolecule filler | 4-20 parts; |
| antioxidant | 0.01-5 parts; | step 2: dissolving the starch or the colloid and the micromolecule filler in water at 40° C. to 60° ° C. to form a first mixture, and then cooling the first mixture to 0-30° C.;
step 3: adding an aqueous phase antioxidant into the first mixture in step (2), and stirring at 0° to 30° C. until the aqueous phase antioxidant is completely dissolved in the first mixture to obtain the second mixture;
step 4: adding an oil phase antioxidant into the conjugated linoleic acid glyceride, and stirring at 10-25° C. until the oil phase antioxidant is completely dissolved to obtain an oil phase;
step 5: adding the oil phase into the second mixture to form a third mixture, controlling the temperature of the third mixture between 0-30° C., shearing and emulsifying the third mixture for 0.5 hour to 2 hours, and then homogenizing for 1 time to 3 times at 40-120 MPa to obtain an emulsion; and
step 6: performing spray drying on the emulsion prepared in step (5) at an air inlet temperature of 90-230° C., and an air outlet temperature of 50-110° C.,
wherein the starch comprises native starch or modified starch,
the modified starch is selected from acid-modified starch, oxidized starch, starch acetate, phosphate acetate, cross-linked starch, hydroxypropyl starch, and pregelatinized starch, and mixtures thereof; and
the colloid is selected from xanthan gum, gelatin, Arabic gum, and mixtures thereof,
wherein the microsencapsulated conjugated linoleic acid glyceride powder has an embedding rate of 98.1% to 99.5% at an oil load of 70%.

2. The method according to claim 1, wherein the micromolecule filler in step (1) is selected from glucose syrup, maltodextrin, maltooligosaccharide, fructooligosaccharide, resistant dextrin, solid corn syrup, cyclodextrin, and mixtures thereof.

3. The method according to claim 1, wherein the antioxidant in step (1) comprises the aqueous phase antioxidant, the oil phase antioxidant, or both, wherein the aqueous phase antioxidant is selected from sodium ascorbate, ascorbic acid, citric acid, sodium citrate and ascorbyl palmitate; and the oil phase antioxidant is selected from d-α tocopherol, dl-α tocopherol, mixed tocopherol, rosemary extract, phospholipid, butylated hydroxyanisole, antioxidant 264, tert-butylhydroquinone and the mixture thereof.

4. The method according to claim 1, wherein, in step 2, the dissolving is carryout out in water at 50° C. to 60° C., and then cooled to 0-20° C.; in step 3, the stirring is carried out at 0-20° C.; in step (4), the stirring is carried out at 0-20° C.; in step (5), the temperature of the third mixture is at 0-20° C., shearing and emulsifying is carried out for 0.5-1.5 hours, and homogenizing is carried out for 1-3 times at 45-90 MPa to obtain the emulsion; and in step (6), the air inlet temperature is 110-180° C., and the air outlet temperature is 70-100° C.

5. The method according to claim 1, further comprising a step of adding an anti-caking agent into the microencapsulated powder prepared in step 5, wherein the anti-caking agent is selected from silicon dioxide, calcium silicate, tricalcium phosphate and sodium dihydrogen phosphate, and mixtures thereof.

6. The method according to claim 5, wherein the dosage of the anti-caking agent does not exceed 2% of a mass of the microencapsulated powder.

7. The method according to claim 1, wherein the conjugated linoleic acid glyceride in the raw materials is pre-treated by a pre-treatment method that includes the steps of:
mixing activated carbon of 160-200 mesh with crude conjugated linoleic acid glyceride according to a mass ratio of 1:80-120 at an operating temperature of 30-45° C., stirring for 0.5-5 hours for adsorption, and then filtering the same with 280-mesh filter cloth; and
centrifuging filtered grease at 4000-6000 rpm for 15 minutes to 30 minutes at 10-25° C., and
obtaining a supernatant transparent liquid comprising the conjugated linoleic acid glyceride.

* * * * *